United States Patent
Ash, III

(10) Patent No.: US 8,269,974 B2
(45) Date of Patent: Sep. 18, 2012

(54) INTERFEROMETRIC CHEMICAL SENSOR ARRAY

(75) Inventor: William M. Ash, III, Largo, FL (US)

(73) Assignee: University of South Florida, Tampa, FL (US)

( * ) Notice: Subject to any disclaimer, the term of this patent is extended or adjusted under 35 U.S.C. 154(b) by 490 days.

(21) Appl. No.: 12/488,982

(22) Filed: Jun. 22, 2009

(65) Prior Publication Data

US 2009/0316158 A1   Dec. 24, 2009

Related U.S. Application Data

(60) Provisional application No. 61/074,724, filed on Jun. 23, 2008.

(51) Int. Cl.
*G01J 3/45* (2006.01)

(52) U.S. Cl. ....................................................... 356/451

(58) Field of Classification Search .................. 356/451, 356/480; 997/880, 881
See application file for complete search history.

(56) References Cited

U.S. PATENT DOCUMENTS

| | | | | |
|---|---|---|---|---|
| 4,417,815 A | * | 11/1983 | Murray et al. | 356/480 |
| 4,594,510 A | * | 6/1986 | Brown et al. | 250/339.13 |
| 4,849,637 A | * | 7/1989 | Cerff et al. | 250/345 |
| 4,930,862 A | | 6/1990 | Miers et al. | |
| 5,004,914 A | | 4/1991 | Vali et al. | |
| 5,262,842 A | | 11/1993 | Gauglitz et al. | |
| 5,337,376 A | | 8/1994 | Ravetti et al. | |
| 5,345,306 A | * | 9/1994 | Ichimura et al. | 356/451 |
| 5,805,063 A | | 9/1998 | Kackman | |
| 6,493,090 B1 | | 12/2002 | Lading et al. | |
| 6,603,560 B1 | | 8/2003 | Islam | |
| 6,657,731 B2 | * | 12/2003 | Tapalian et al. | 356/480 |
| 6,975,944 B1 | | 12/2005 | Zenhausern | |
| 7,068,372 B1 | | 6/2006 | Trisnadi et al. | |
| 7,095,010 B2 | * | 8/2006 | Scherer et al. | 250/227.11 |
| 7,097,973 B1 | | 8/2006 | Zenhausern | |
| 7,248,357 B2 | * | 7/2007 | Servaites et al. | 356/306 |
| 7,289,221 B2 | * | 10/2007 | Wang et al. | 356/477 |

(Continued)

FOREIGN PATENT DOCUMENTS

GB    2385915 A    9/2003

(Continued)

OTHER PUBLICATIONS

Xing-Jiu Huang, et al., Chemical Sensors Based on Nanostructured Materials, Science Direct, Sensors and Actuators B, 2007, vol. 122, pp. 659-671.

(Continued)

*Primary Examiner* — Tarifur Chowdhury
*Assistant Examiner* — Jonathan Hansen
(74) *Attorney, Agent, or Firm* — Nilay J. Choksi; Anton J. Hopen; Smith & Hopen, P.A.

(57) ABSTRACT

The device is a gas/vapor/aerosol/particulate sensor with a receiver/transmitter option. This optical MEMS device is designed to be a self-contained optical bench, integrating of an entire interferometer into a MOEMS 'optical bench' system-on-a-chip, and includes multiplexed optical path sensors. The sensing structures consist of laser sources, semiconductor photo detectors, refractive/reflective optical elements, and specialized optical transmission paths. Each individual laser source and photodiode is an optical path sensor with a particular 'functionalization.' These sensing arm functionalizations are sensitive to unique chemical signatures and as a result can recognize and report various chemical agents present in the ambient environment.

13 Claims, 6 Drawing Sheets

U.S. PATENT DOCUMENTS

| | | | |
|---|---|---|---|
| 7,292,342 B2 * | 11/2007 | Zaugg | 356/451 |
| 7,426,035 B2 * | 9/2008 | Shpantzer | 356/451 |
| 7,502,118 B2 * | 3/2009 | Shpantzer | 356/451 |
| 7,697,796 B2 * | 4/2010 | Kashyap et al. | 385/12 |
| 7,903,252 B2 * | 3/2011 | Larsen et al. | 356/451 |
| 2006/0066866 A1 | 3/2006 | Wang et al. | |
| 2006/0066867 A1 | 3/2006 | Beausoleil | |
| 2006/0072642 A1 | 4/2006 | Wang et al. | |
| 2006/0192974 A1 | 8/2006 | Li | |
| 2006/0262322 A1 | 11/2006 | Brooks | |
| 2007/0097694 A1 | 5/2007 | Faase et al. | |
| 2007/0279638 A1 | 12/2007 | Choo et al. | |
| 2007/0285761 A1 | 12/2007 | Zhong et al. | |

FOREIGN PATENT DOCUMENTS

| | | |
|---|---|---|
| WO | WO 2007/136779 A2 | 11/2007 |

OTHER PUBLICATIONS

Jongin Hong, et al., A Mach-Zehnder Interferometer Based on Silicon Oxides for Biosensor Applications, Science Direct, Analytica Chimica Acta, 2006, vol. 573-574, pp. 97-103.

Chuan Pu, et al., Surface Micro-Machined Optical Coherent Detection System with Ultra-High Sensitivity, Sensors and Actuators, 1999, vol. 78, pp. 36-40.

L.M. Lechuga, et al., Integration of Bio, Nano, Micro and Cogno in Biosensor Devices for Human Health Applications, Superficies y vacio, 2005, vol. 18, No. 4., pp. 1-6.

Dainesi, P., et al., CMOS Compatible Fully Integrated Mach-Zehnder Interferometer in SOI Technology, IEEE Photonics Technology Letters, 2000, vol. 12, No. 6, pp. 660-662.

Abeysinghe, D., et al., A Novel MEMS Pressure Sensor Fabricated on an Optical Fiber, IEEE Photonics Technology Letters, 2001, vol. 13, No. 9, pp. 993-995.

Porte, H., et al., Imbalanced Mach-Zehnder Interferometer Integrated in Micromachined Silicon Substrate for Pressure Sensor, Journal of Lightwave Technology, 1999, vol. 17, No. 2, pp. 229-233.

Yamamoto, G., et al., Determination of Aerosol Size Distribution from Spectral Attenuation Measurements, Applied Optics, 1969, vol. 8, No. 2, pp. 447-453.

Yu, K., et al., Micromachined Fourier Transform Spectrometer on Silicon Optical Bench Platform, Sensors and Actuators A, 2006, vol. 130-131, pp. 523-530.

Baker, K. et al., High-Speed Horizontal-Path Atmospheric Turbulence Correction with a Large-Actuator-Number Microelectromechanical System Spatial Light Modulator in an Interferometric Phase-Conjugation Engine, Optics Letters, 2004, vol. 29, No. 15, pp. 1781-1783.

Kovacs, Micromachined Transducers Sourcebook, Optical Tranducers, 1998, pp. 484-507.

Hariharan, Optical Interferometry, Elsevier Science Academic Press, 2003.

Ash, Chemical Agent Micro Sensor Chip, MicroMech Optical, 2008, pp. 1-23.

Ash, MIOBS-MOEMS-Based Interferometric Optical Bench System, Technical Entrepreneurship/Business Plan Development, 2008, pp. 1-11.

* cited by examiner

INTERFEROMETRIC CHEMICAL SENSOR ARRAY

PRIORITY CLAIM

This invention claim priority to U.S. Provisional Patent Application Ser. No. 61/074,724 field Jun. 23, 2008 entitled "MOEMS-Based Interferometric Optical Bench System" the specification of which is incorporated herein by reference.

STATEMENT OF GOVERNMENT INTEREST

This invention was made with Government support under Grant No. DE-0221681 awarded by the National Science Foundation. The Government has rights in the invention.

FIELD OF INVENTION

This invention relates to a device designed to rapidly detect harmful agents in the air. Specifically, the invention entails using interferometers in sensing devices.

SUMMARY OF INVENTION

Non-MOEMS (Micro-Optical Electro-Mechanical System) chemical gas vapor sensors are designed to detect agents affecting the nervous system, the skin and mucous membranes, and the blood. These devices utilize a spectroscopic technique that produces sensors that are bulky, heavy, and difficult to transport. Moreover, these devices are high power consumption sensors, requiring large power sources, further increasing size and weight.

Interferometry is important for use in many precision sensing applications including, but not limited to, physical signature identification of gases and liquids. MOEMS interferometers have consisted of discrete MOEMS devices, such as a detector serving as a 'part' in a larger macro-scale system design. State of the art devices still use off-board sources, detectors and fiber optics.

Applications for MIOBS are important to researchers, and a significant value is placed on the successful integrated miniaturization of a complete stand-alone optical system-on-a-chip. Broader impacts of this idea include immediate applications where small inexpensive gas and fluid sensors are needed to fit in small places. Alternative embodiments include not only precise position sensing of mirror displacement in micromechanical systems, but also implementations such as strain gauges and stand alone ring laser gyroscopes free from the physical, engineering and production constraints associated with proof-mass systems.

Seeing an identifiable need, this invention discloses integration of an entire interferometer into a MOEMS 'optical bench' system-on-a-chip. This optical MEMS device is designed to be a self-contained optical bench on a single chip with multiplexed optical path sensors. The sensing structures consist of laser sources, semiconductor photo detectors, refractive/reflective optical elements, and specialized optical transmission paths. Laser sources and their photo detectors are grown on the substrate or can be bonded into place as drop-in dies. In some embodiments, the device utilizes micron/nano-scale integration; space, weight, power, on-board conditioning, processing and transmitter/receiver electronics, element proximity and optical alignment, with scale sizes approaching perceived 'ultimate' physical constraints such as the diffraction limit.

This invention comprises a MOEMS-based split beam interferometer, of the Mach-Zehnder or Michelson type, in order to sense optical path length differences between an exposed/vented object beam test arm and a 'sealed' reference beam arm. The interferometer comprises an optical coupler that bonds to the source input line providing the laser source input light, a beam splitter which splits the input signal into a sensing beam and a reference beam and then provides a path for the sense and reference beam to recombine thus producing the interferometers characteristic superposition of waveforms and the ability to easily detect small shifts in their output fringe patterns and convert this fringe shift into a detectable electric signal. The reference arm is an optical replication of the sense arm in its initial, undisturbed, null state. The sense arm however is open to the ambient environment and the functionalization of its optical path is designed such that it reacts in the presence of certain chemical species, which are indicative of chemical agents, herein termed 'chemical signatures'. Both the sensing and the reference arms are optical paths, such as light guides, constructed with standard micromachining techniques, such as silicon fabrication methods and have mirror structures at the end of their arms that reflect the light signal back to the beam splitter which recombines the two beam causing waveform superposition and the subsequent interference fringing in the detector arm. When the interferometer is stabilized in its initial state, the detector registers this initial input level which the system's electronics registers and monitors. When a change in the optical path of the sense arm takes place, as a result of chemically reacting with the species for which it is sensitive, the interference fringe created by the waveform superposition shifts and this shift in the interference fringe at the detector results in a change in the detector's electrical output level which the system flags as a positive reading and compares that signal to the status of the rest of the sensing array and the system's state.

An exemplary sensor according to an embodiment of the invention may encompass an area of approximately one square inch, and is encased in a polymer that makes it resistant to environmental extremes. The device is designed to rapidly detect harmful chemical agents in the air, generally of minute volumes of the targeted chemical measured in parts per trillion, by replacing current devices with a single, small, portable microchip sensor capable of being integrated into a uniform or personal equipment. The construction of the device is based on MOEMS interferometer technology that utilizes lasers incorporated on a silicon chip array to receive, detect, and transmit results. The device may be multiplexed to detect multiple chemical agents simultaneously, and possesses a receiver/transmitter option.

Conductive bonding pads are placed for the connection of electronic power, ground and signal. Standard silicon wafer processing technology is utilized.

The sensing functionalization may be comprised of nanowires, aerogels, 'aero-corals', crystal matrices, particulate/catalyst meshes, amorphous materials, treated fabrics, or other known means known in the art, and may be implemented for reasons such as ease of fabrication, better optical performance, and better sensitivity to the desired chemical signature. The surfaces and chemical characteristics of these nanostructures are chosen and engineered such that they provide active sites, such as a strong alkali, for the target chemical agent to bind to or react with. These chemical sites are also designed and chosen such that the change due to the chemical reaction causes a sufficient change in the optical path to be reliably detected, is well behaved from a systems engineering approach and is not easily spoofed by spurious signatures in the ambient environment.

The sensitivity of an embodiment of the invention may range from parts per billion to parts per trillion of the target agent. The described embodiment is small, lightweight, and convenient to carry. It is contemplated that the device may be used with automotive safety and control systems, industrial control and safety systems, home and building sensing and control, fluidic sensors, agricultural monitors, vibration sensors, magnetometers, and position sensors. The device may also be used in a Sagnac ring interferometer for rotation sensing.

An embodiment of the invention comprises an interferometric, single chip sensor having a laser, a first optical path having a functionalized sense arm open to an ambient environment, the sense arm reactive to a preselected chemical signature such as chlorine, cyanogens, sulfide, phosphorus, fluoride or the like. The sense arm may be reactive to a single chemical signature or may be relative to a plurality of chemical signatures. The sensing functionalization of the sense arm may include, but is not limited to, nanowires, aerogels, aerocorals, crystal matrices, particulate meshes, catalyst meshes, amorphous materials and treated fabrics. The sense arm may include chemically reactive nanostructures open to the ambient environment while the reference arm contains chemically reactive nanostructures sealed from the ambient environment.

A second optical path having a reference arm is sealed from the ambient environment using glass or nitride. A beam splitter sends light emitted from the laser to both the first and second optical paths whereby the chemical signature reacting at the functional sense arm changes the first optical path length relative to the second optical path length.

A beam recombiner creates a superposition of sense and reference beams yielding interference fringes responsive to the change in the first optical path length and a photodetector converts the shift into a detectable electrical signal.

A wireless transmitter communicatively coupled to the photodetector may be provided. The wireless transmitter broadcasts data responsive to a predetermined value of the detectable electrical signal converted by the photodetector.

An alternative embodiment of the invention provides for a chemical vapor sensor array. The array includes multiple interferometric sensors on a single chip, each sensor specific to a preselected chemical signature. The identity of the chemical vapor is logically derived by one or more electrical signals from the sensors. The derivation may be made not only from the positive signals of one or more sensors, but also from the absence of a signal from one or more sensors.

A logic gate integral to the chip may be provided wherein the logic gate activates a signal responsive to an identification of the chemical vapor. Alternatively or in conjunction with the integral logic gate, a wireless transmitter may forward the one or more electrical signals from the sensors to a remote logic processor for deriving the identity of the chemical vapor. A remote receiver may receive the forwarded signal to coordinate a proper response to the chemical detection.

As the reactive nature of the sensing arm may lend itself to a limited life-span, an embodiment of the invention anticipates that the chemical vapor sensor array is a single use device whereby upon detection the electrical signals received from the sensors, the state of the electrical signals is maintained for confirmation of the results. A timestamp value may be stored in conjunction with the firing of the electrical signals.

Each sensor may be uniquely specific to at least one preselected chemical signature to collectively identify a chemical vapor. Alternatively, redundant sensors for the same chemical signature may be provided on a single chip to mitigate the possibilities of false positive signals.

In yet another alternative embodiment of the invention the identity of the chemical vapor is logically derived by one or more electrical signals from the sensors against an empirically established matrix of known chemical vapor signal patterns. Alternatively stated, a library of fingerprint signal collections is generated by exposing the array to known chemical vapors.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Embodiments of the present invention may include gas/vapor/aerosol/particulate interferometric sensors with a receiver/transmitter options. All structures in the interferometric sensor unit are intended to be fabricated with standard silicon processing techniques (i.e. CMOS), including wafer level bonding and bulk micromachining. The sensor is designed to rapidly detect harmful chemical agents in the air with a single, small, portable microchip sensor, using MOEMS interferometer technology that utilizes lasers incorporated on a silicon chip array to receive, detect, and transmit results. Bonding pads are used for the laser source input and photodetector output. Crystal planes are envisioned, as well as corner reflectors. This optical MEMS device is designed to be a self-contained optical bench on a single chip with multiplexed optical path sensors. The sensing structures consist of laser sources, semiconductor photo detectors, refractive/reflective optical elements, and specialized optical transmission paths. Embodiments of the invention may utilize a single lithium coin battery to provide power for up to one year.

Figure 1:
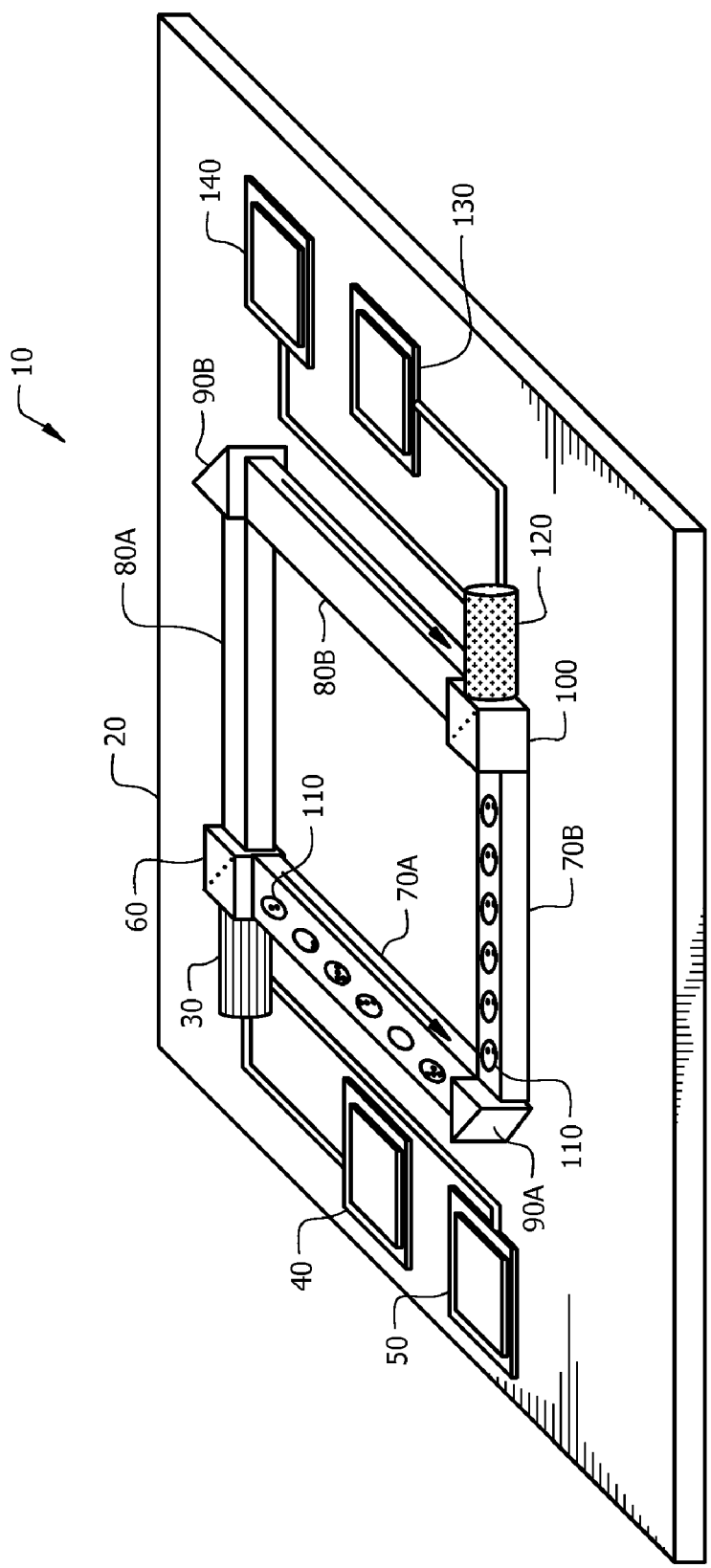
FIG. 1 is an elevated, isometric conceptual view of an embodiment of the invention for detecting chemical vapor signatures using Mach-Zehnder-type interferometer.

Turning to FIG. 1, Michelson-type topology sensor 10 comprises a substrate 20 upon which various components are affixed, dropped in, or manufactured in situ. Laser 30 is powered by laser power source 40 and controlled by laser control 50. Beam splitter 60 splits light emitted from laser 30 down sense arm 70A-B and reference arm 80A-B. Corner reflector 90A angles beam from sense arm 70A to sense arm 70B. Corner reflector 90B angles beam from reference arm 80A to reference arm 80B. Sense arm 70A-B is functionalized to react to a preselected chemical signature in the ambient environment. Portals 110 provide access to ambient vapors. Reference arm 80A-B is conversely sealed from the ambient environment and acts as a control. A chemical vapor having the preselected chemical signature reacts at the functional sense arm 70A-B which changes the optical path length of sense arm 70A-B relative to reference arm 80A-B. Beam recombiner 100 creates a superposition of sense and reference beams yielding interference fringes responsive to the change in optical path length. Photodetector 120 converts the shift into a detectable electrical signal. Photodetector power source 130 and photodetector control 140 are respectively electrically and communicatively coupled to photodetector 120.

Figure 2:
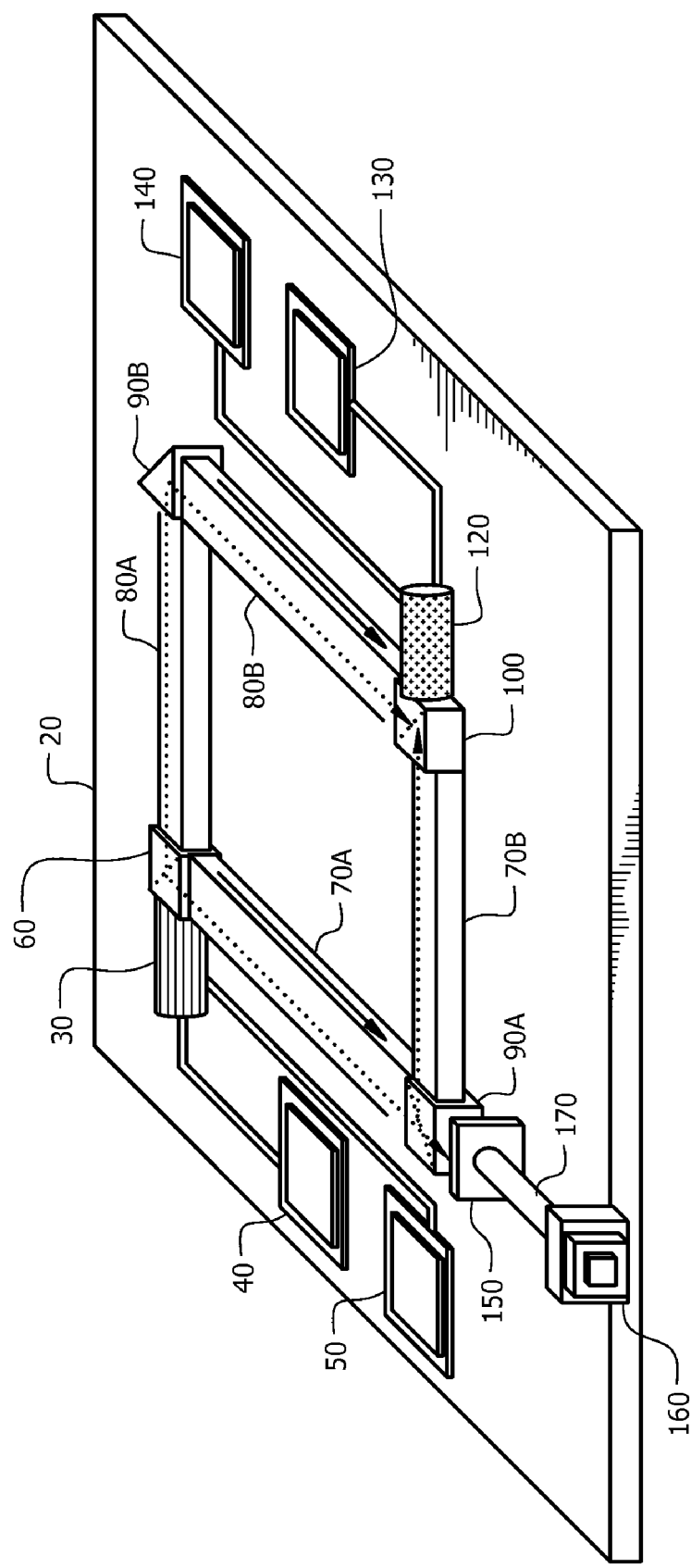
FIG. 2 is an elevated, isometric conceptual view of an embodiment of the invention for detecting mechanical movement using Mach-Zehnder-type interferometer.

In FIG. 2, an embodiment of the invention employs a movable mirror 150 and a sense arm 160 open to the environment. Moveable mirror 150 aligned to sense arm 70A-B utilizes mechanical linkages 170 and allows the optical path length to change in the sense arm 70A-B. This causes a fringe pattern shift detected by photodetector 120.

Figure 3:
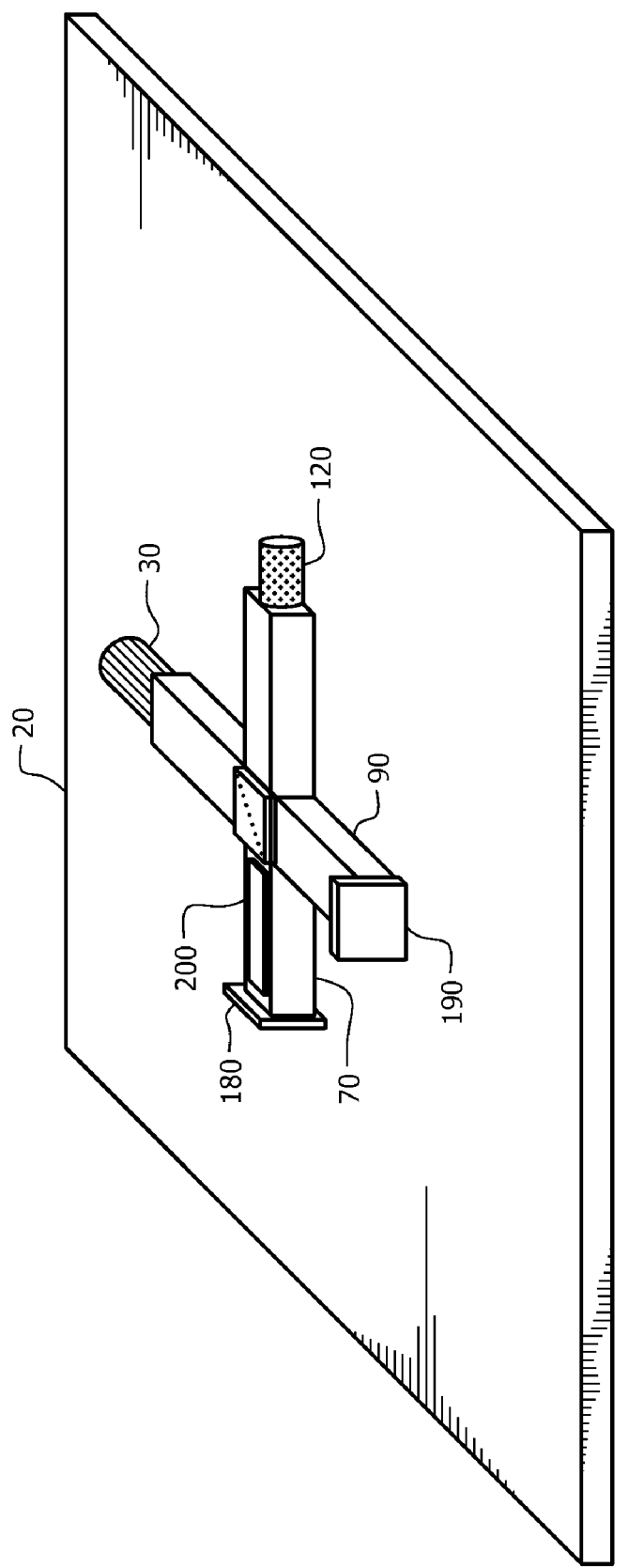
FIG. 3 is an elevated, isometric conceptual view of an embodiment of the invention for detecting chemical vapor signatures using Michelson-type interferometer.
Figure 4:
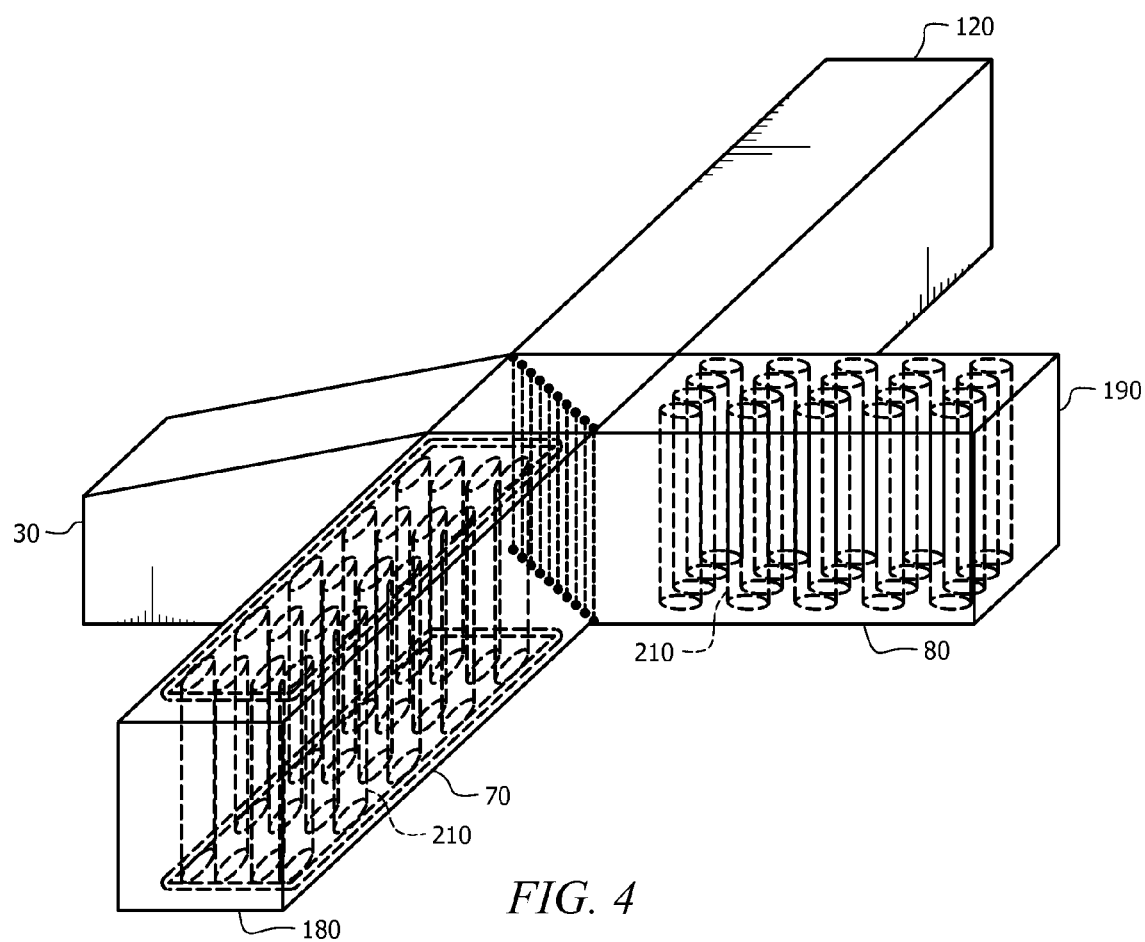
FIG. 4 is an elevated, isometric conceptual view of an embodiment of the invention depicting a Michelson-type interferometer sensor with a functionalization scheme in the open ambient sensing arm that is replicated in the sealed reference arm.

In FIG. 3, an alternative embodiment of the invention is shown utilizing Michelson topography wherein first mirror 180 at the end of sense arm 70 and second mirror 190 at the end of reference arm 80 reflect a beam from laser 30. Sensing window 200 in sense arm 70 reacts to chemical signatures which are detected by photodetector 120. In FIG. 4, forests of functional nanowires 210 are provided within both sense arm 70 and reference arm 80. However, functional nanowires 210 are sealed from the ambient environment in reference arm 80.

Figure 5:
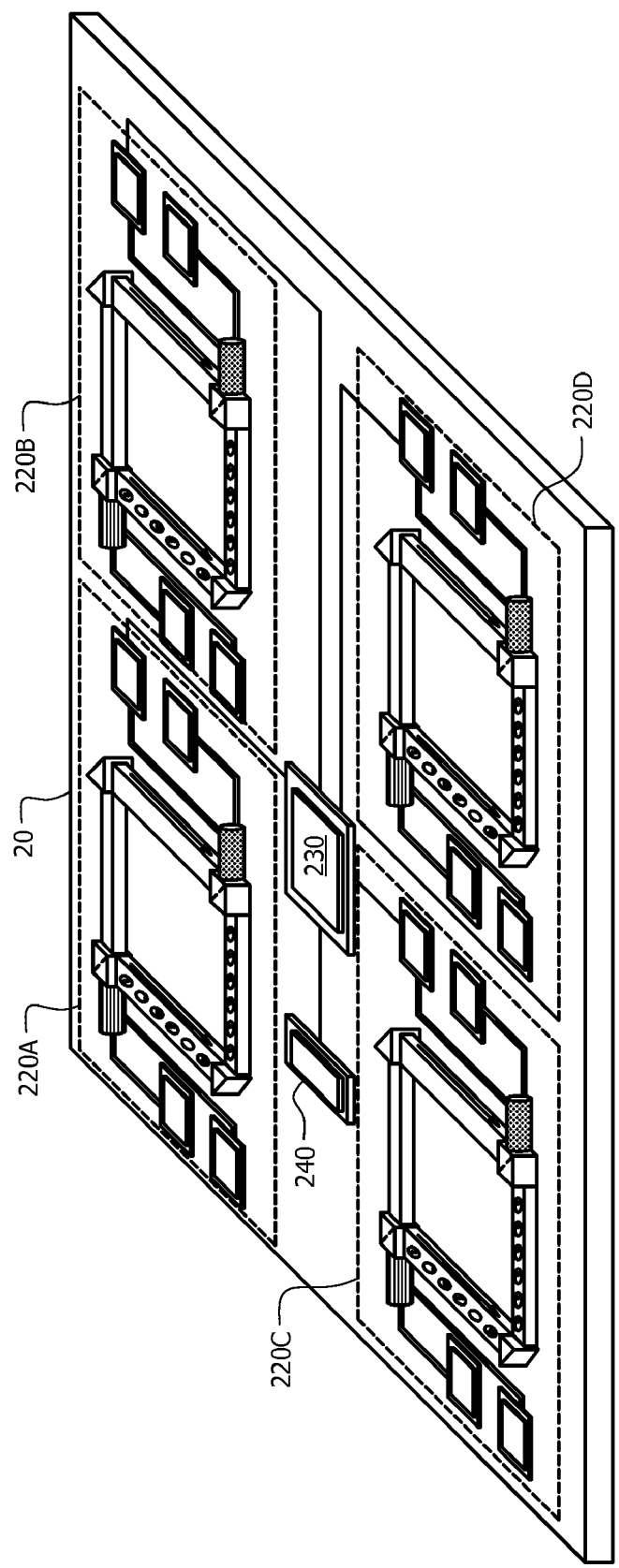
FIG. 5 is an elevated, isometric conceptual view of an embodiment of the invention comprising an array of Mach-Zehnder-type interferometer sensors on a single chip.

In FIG. 5, an array of interferometer sensors 220A-D are provided on single chip 20. Sensor 220A is specific to the detection of chlorine. Sensor 220B is specific to the detection of cyanogens. Sensor 220C is specific to the detection of sulfide. Sensor 220D is specific to the detection of phosphorous. Responsive to exposure to the ambient environment containing nerve agent VX, only sensors 220C and 220D generate signals to logic gate 230. Logic gate 230 compares the received signals to Table 1 (reproduced below) and generates a wireless transmission via transmitter 240 that the presence of nerve agent VX has been detected by the array.

Figure 6:
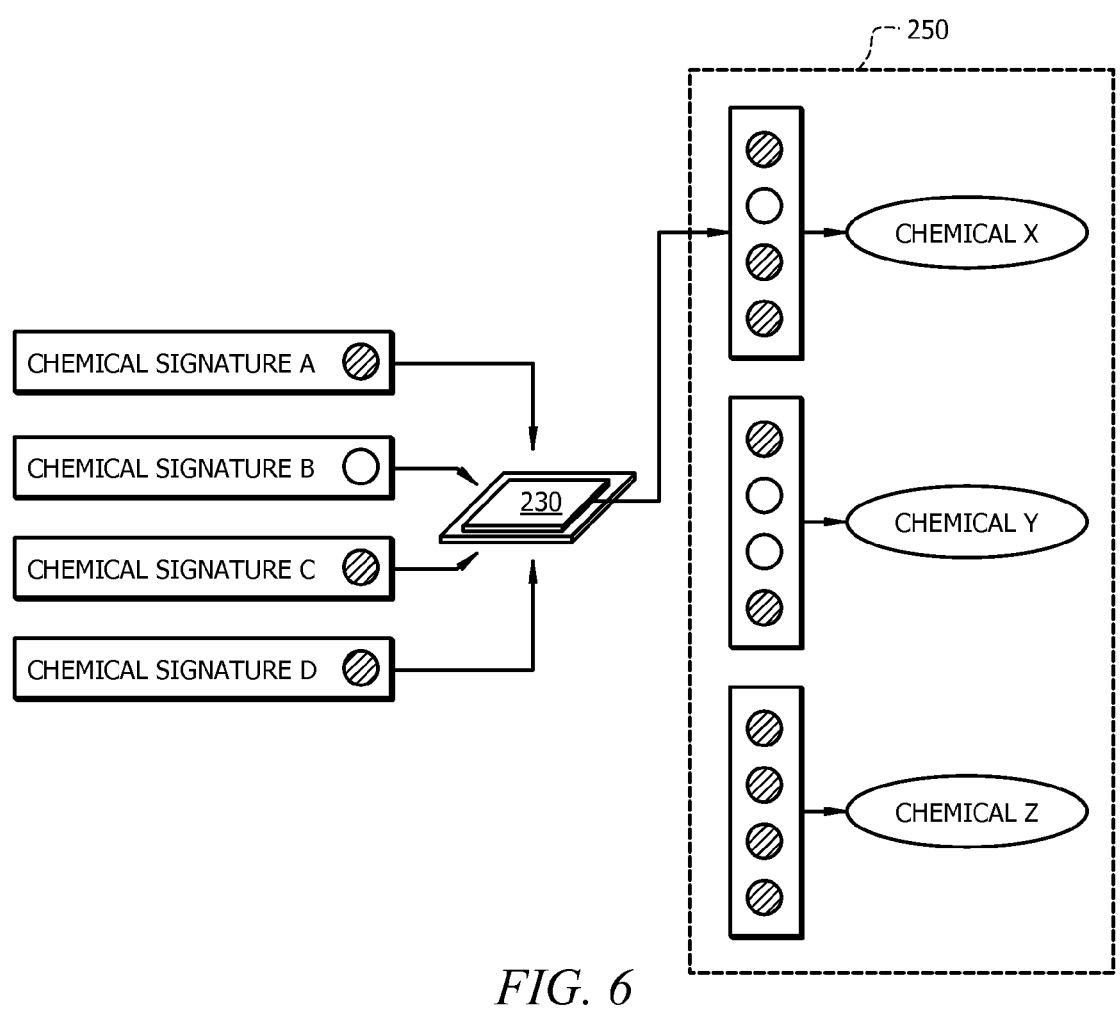
FIG. 6 is a diagrammatic view of a logical process for deriving a chemical identity from a plurality of interferometer sensor readings.

FIG. 6 shows a conceptual representation of the logical process wherein four (4) sensors indicate positive chemical signatures A, C and D. Logic gate 230 compares the Boolean results for each chemical signature in combination against lookup table 250 to resolve the presence of Chemical X.

Each individual laser source and photodiode is an optical path sensor with a particular 'functionalization,' as seen in FIG. 4. The sensing functionalization is depicted as a forest of nanowires of optical grade silica. These chemical sites are also designed and chosen such that the change due to the chemical reaction causes a sufficient change in the optical path to be reliably detected, is well behaved from a systems engineering approach and is not easily spoofed by spurious signatures in the ambient environment.

In addition to chemical functionalization, biological and other functionalizations are possible. The success of other functionalizations are based upon the capability of MEMS fabrication technology, optical sensing constraints, and chem/bio agent physio-chemical characteristics. Features such as thermal elements can also be added to optimize sensitivity and packing arrangements can be made to resist extreme environments. For instance, in one possible packing arrangement, the sensor rests on a plastic base enclosed in a translucent polymer to make it resistant to ambient environment extremes.

The laser sources and photo detectors are grown on the standard silicon wafer processor or bonded into place as drop-in dies. Conductive bonding pads are then attached for the connection of electronic power, ground and signal. Each individual laser source and photodiode is an optical path sensor with a particular 'functionalization.' These sensing arm functionalizations are sensitive to unique chemical signatures and as a result can recognize various chemical agents present in the ambient environment. The device may also utilize laser source signals via light guides that the sensor inputs can opto-mechanically couple onto and also provides the electrical routing for the fringe detect signal to the output circuitry. Note that the array consists of as many different types of functionalizations as necessary to cover a full "suite" of chemical signatures. This detection matrix is depicted in Table 1.

TABLE 1

Chemical Agent Signatures

| Agent | Name | Primary Species Signature | Secondary signature | Detection Comments |
| --- | --- | --- | --- | --- |
| $Cl_2$ | Chlorine | Chlorine | | Halide substitution (Br, I) |
| CK | Cyanic Chloride | Cyanogen | Chloride | Precursor to sulfonyl cyanide; Halogen substitution CNBr |
| AC | Hydrogen Cyanide | Cyanogen | | Reacts with alkenes |
| HD | Sulfur Mustard | Sulfide | Chloroethyl | Sulfur reaction with silver |
| GA | Tabun | Phosphorus | | Reacts with strong alkali |
| GB | Sarin | Phosphorus | Fluoride | Reacts with strong alkali |
| VX | Nerve Agent | Phosphorus | Sulfide | Reacts with OH group |
| CG | Phosgene | Chloride | | Halide substitution (Br, I) |

The invention uses split beam pathways to detect biological or chemical agents, but permits the detector to highly compact, thereby allowing a user to wear the device. Upon sensing chemical agents, the device alerts personnel to their presence and type. The alerts are both in the proximity of the device via an audible alarm and remotely to a tactical warfighter information network (WIN-T) net via intelligent transmitter/receiver link. This capability is a result of current fabrication technology which allows for receiver/transmitter sections and control electronics to be placed on-board and adjacent to the sensor arrays. The device can also be multiplexed to detect more than one chemical agent, and possesses a receiver/transmitter option.

Soldiers can wear it on helmets, clothing, and armbands or it can be attached to moving vehicles, planes, and trains. The device can easily be modified to detect airborne biological warfare agents that may be present. The device can detect chemical signatures in seconds.

What is claimed is:

1. A chemical vapor sensor array comprising:
a plurality of interferometric sensors on a single chip, each sensor specific to a preselected chemical signature, each sensor comprising:
   a laser source;
   a first optical path having a functionalized sense arm open to an ambient environment and reactive to the preselected chemical signature;
   a second optical path having a reference arm sealed from the ambient environment;
   a beam splitter sending light emitted from the laser to both the first and second optical paths whereby the chemical signature reacting at the functional sense arm changes the first optical path length relative to the second optical path length;
   a beam recombiner creating a superposition of sense and reference beams yielding interference fringes responsive to the change in the first optical path length; and
   a photodetector for converting the interference fringes into a detectable electrical signal,
   whereby the identity of the chemical vapor is logically derived by one or more electrical signals from the sensors; and
   a logic gate integral to the chip, the logic gate activating a signal responsive to an identification of the chemical vapor.

2. The array of claim 1 further comprising a wireless transmitter to forward the one or more electrical signals from the sensors to a remote logic processor for deriving the identity of the chemical vapor.

3. The array of claim 1 further comprising a wireless transmitter to forward the signal to a remote receiver.

4. The array of claim 1 wherein the sense arm of at least one sensor on the array is reactive to a plurality of chemical signatures.

5. The array of claim 1 wherein the chemical vapor sensor array is a single use device whereby upon detection the electrical signals received from the sensors the state of the electrical signals is maintained.

6. A chemical vapor sensor array comprising:
a plurality of interferometric sensors on a single chip, each sensor specific to at least one preselected chemical signature to collectively identify a chemical vapor, each sensor comprising:
   a laser;
   a first optical path having a functionalized sense arm open to an ambient environment and reactive to a sensor-specific preselected chemical signature;
   a second optical path having a reference arm sealed from the ambient environment;
   a beam splitter sending light emitted from the laser to both the first and second optical paths whereby the chemical signature reacting at the functional sense arm changes the first optical path length relative to the second optical path length;
   a beam recombiner creating a superposition of sense and reference beams yielding interference fringes responsive to the change in the first optical path length; and
   a photodetector for converting the interference fringes into a detectable electrical signal;
   a logic gate integral to the chip, the logic gate deriving the identity of the chemical vapor by one or more electrical signals from the sensor, the logic gate subsequently activating a signal responsive to an identification of the chemical vapor.

7. A chemical vapor sensor array comprising:
a plurality of interferometric sensors on a single chip, each sensor specific to a unique preselected chemical signature, each sensor comprising:
   a laser;
   a first optical path having a functionalized sense arm open to an ambient environment and reactive to the sensor's unique preselected chemical signature;
   a second optical path having a reference arm sealed from the ambient environment;
   a beam splitter sending light emitted from the laser to both the first and second optical paths whereby the chemical signature reacting at the functional sense arm changes the first optical path length relative to the second optical path length;
   a beam recombiner creating a superposition of sense and reference beams yielding interference fringes responsive to the change in the first optical path length; and
   a photodetector for converting the interference fringes into a detectable electrical signal,
   whereby the identity of the chemical vapor is logically derived by one or more electrical signals from the sensors against an empirically establish matrix of known chemical vapor signal patterns.

8. The array of claim 6 wherein the sensing functionalization of the sense arm is selected from the group consisting of nanowires, aerogels, aero-corals, crystal matrices, particulate meshes, catalyst meshes, amorphous materials and treated fabrics.

9. The array of claim 6 wherein the functionalized sense arm further comprises chemically reactive nanostructures open to the ambient environment and the reference arm further comprises chemically reactive nanostructures sealed from the ambient environment.

10. The array of claim 6 further comprising a wireless transmitter communicatively coupled to the photodetector, the wireless transmitter broadcasting data responsive to a predetermined value of the detectable electrical signal converted by the photodetector.

11. The array of claim 7 wherein the sensing functionalization of the sense arm is selected from the group consisting of nanowires, aerogels, aero-corals, crystal matrices, particulate meshes, catalyst meshes, amorphous materials and treated fabrics.

12. The array of claim 7 wherein the functionalized sense arm further comprises chemically reactive nanostructures open to the ambient environment and the reference arm further comprises chemically reactive nanostructures sealed from the ambient environment.

13. The array of claim 7 further comprising a wireless transmitter communicatively coupled to the photodetector, the wireless transmitter broadcasting data responsive to a predetermined value of the detectable electrical signal converted by the photodetector.

* * * * *